United States Patent [19]

Vora et al.

[11] Patent Number: 5,672,795
[45] Date of Patent: Sep. 30, 1997

[54] BALANCED ALKYLATION FEED FROM ETHERIFICATION AND ISOMERIZATION

[75] Inventors: Bipin V. Vora, Darien; Tamotsu Imai, Mount Prospect; Peter R. Pujado, Palatine, all of Ill.

[73] Assignee: UOP, Des Plaines, Ill.

[21] Appl. No.: 533,291

[22] Filed: Sep. 25, 1995

Related U.S. Application Data

[63] Continuation of Ser. No. 222,991, Apr. 5, 1994, which is a continuation-in-part of Ser. No. 998,172, Dec. 29, 1992, abandoned.

[51] Int. Cl.$^6$ .................................................. C07C 41/05
[52] U.S. Cl. .................... 585/332; 585/331; 585/709; 585/714; 568/697
[58] Field of Search ............................ 585/332, 331, 585/709, 714; 568/697

[56] References Cited

U.S. PATENT DOCUMENTS

| | | | |
|---|---|---|---|
| 4,270,929 | 6/1981 | Dang Vu et al. | 44/449 |
| 4,440,871 | 4/1984 | Lok et al. | 502/214 |
| 4,503,282 | 3/1985 | Sikkenga | 585/671 |
| 4,581,474 | 4/1986 | Hutson et al. | 568/687 |
| 4,695,560 | 9/1987 | Gattuso et al. | 502/222 |
| 4,734,540 | 3/1988 | Gattuso et al. | 585/276 |
| 4,758,419 | 7/1988 | Lok et al. | 423/306 |
| 4,778,943 | 10/1988 | Sun | 585/671 |
| 4,814,517 | 3/1989 | Trubac | 568/697 |
| 4,814,519 | 3/1989 | Harandi et al. | 568/697 |
| 5,008,466 | 4/1991 | Schleppinghoff et al. | 568/687 |
| 5,157,178 | 10/1992 | Gajada et al. | 568/687 |
| 5,210,327 | 5/1993 | Luebke et al. | 568/687 |

*Primary Examiner*—Glenn Caldarola
*Assistant Examiner*—Bekir L. Yildirim
*Attorney, Agent, or Firm*—Thomas K. McBride; John G. Tolomei

[57] ABSTRACT

An etherification process combines an alkylation zone with a skeletal olefin isomerization zone in an arrangement that rejects isoalkanes and normal alkanes with only minor loss of valuable olefin isomers. The invention also provides a balanced feed to an alkylation zone for the production of high octane gasoline components. This invention can be used to provide ethers and gasoline boiling range alkylates from either $C_4$ or $C_5$ feedstocks. The invention fully utilizes all olefin isomers improve octane and vapor pressure charactristics of the gasoline components.

22 Claims, 1 Drawing Sheet

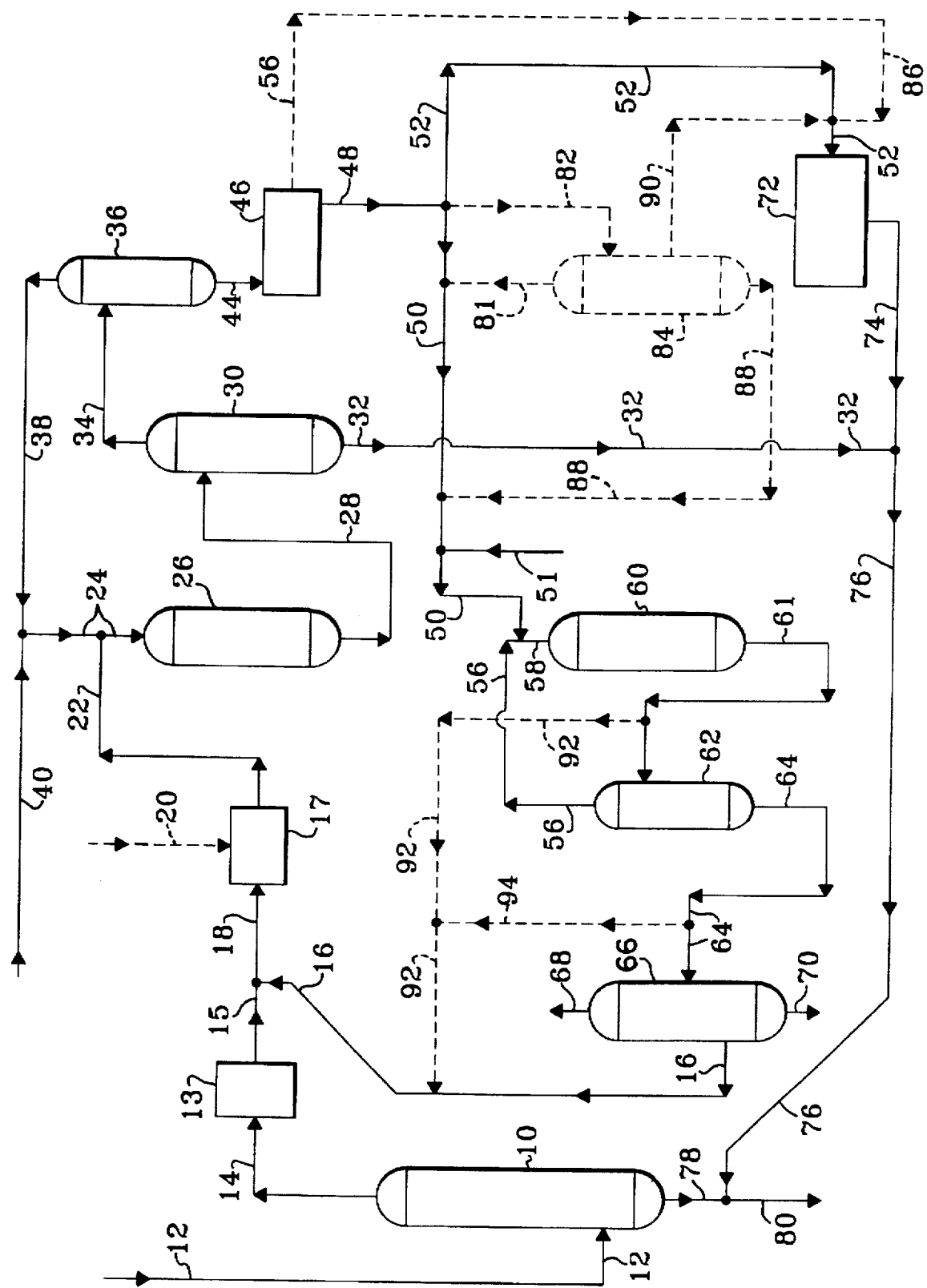

BALANCED ALKYLATION FEED FROM ETHERIFICATION AND ISOMERIZATION

CROSS-REFERENCE TO RELATED APPLICATION

This application is a continuation application of application Ser. No. 08/222,991, filed Apr. 5, 1994, the contents of which are incorporated herein by reference, which is a continuation-in-part of application Ser. No. 07/998,172, filed on Dec. 29, 1992 now abandoned.

FIELD OF THE INVENTION

This invention relates to processes for the production of ethers by the reaction of an alcohol with an isoolefin. More specifically this invention relates to a process for the production of ether and the skeletal isomerization of olefins to provide additional feedstock for the production of ethers and the use of alkylation to remove unconverted saturated material.

BACKGROUND OF THE INVENTION

The production of ethers by the reaction of an isoolefin and an alcohol are well known commercial operations. There are many detailed descriptions of processes for the production of such ethers, in particular, methyl tertiary butyl ether (MTBE) and methyl tertiary amyl ether (TAME). These ethers have long been known as useful octane blending agents for gasoline motor fuels due to their high octane number (RON) of about 120. More recently ether compounds as gasoline blending components have been highly valued as supplying oxygen to meet reformulated gasoline requirements. Processes for the production of MTBE and TAME by reacting methanol with isobutylene or isoamylene, respectfully, are among the most widely known processes for the production of such ethers.

Processes for the production of such ethers have suffered from a shortage of the necessary isoolefins for reaction with the alcohols to provide products. Feedstreams for etherification processes typically consist of a wide variety of olefinic and paraffinic isomers. Processes are known to increase the available feedstock by the dehydrogenation of paraffins and the skeletal isomerization of olefins. Methods for the dehydrogenation of paraffins, in particular isoparaffins, are well known in the art as are processes for the skeletal isomerization of normal olefins to isoolefins. Since the olefinic and paraffinic isomers of any given carbon number have relatively close boiling points, separation of the isomers in an efficient manner to enhance the production of ether as well as the conversion of unreacted products to additional reactants have been difficult. Methods for the various separations have included adsorptive separations as well as extractive distillations. Unreacted isomers have also been used as feed to alkylation units. There is a need for etherification and isomerization process arrangements that simplify the separation of olefinic and paraffinic isomers to provide product and reactants.

SUMMARY OF THE INVENTION

This invention is a process that combines an etherification zone with an alkylation zone and a skeletal olefin isomerization zone in an arrangement that rejects isoalkanes and normal alkanes with only a minor loss of valuable olefin isomers while also providing a balanced feed to the alkylation zone for the production of high octane gasoline components. The narrow boiling point range of many of the $C_4$ and many of the $C_5$ hydrocarbons causes the loss of the valuable alkenes by the necessary rejection of alkanes. It has been discovered that the alkylation zone in combination with the etherification zone will permit consumption of isoalkanes instead of their rejection with the subsequent loss of isomers. In addition, the loss of normal alkenes from the etherification and isomerization loop by venting normal alkanes does not impose economic penalties when the normal alkenes pass to alkylation for the production of more valuable products. For example in the case of $C_4$ hydrocarbons, isobutane has a relatively close boiling point with isobutene and butene-1 and a significant portion of the isobutene and butene-1 is lost from the processing loop by the venting of isobutane for its rejection. By reducing the amount of isobutane rejection in a $C_4$ conversion process for the production of MTBE, isobutene and butene-1 are preserved for reaction to more valuable MTBE or alkylate products. (It is common practice to recycle the normal alkene isomers through the skeletal olefin isomerization zone to obtain additional isoalkene substrate for the etherification reaction.) Again in the case of $C_4$ hydrocarbons, normal butane and butene-2 have relatively close boiling points and rejection of normal butane results in a loss of butene-2. Similarly with $C_5$ hydrocarbons for the production of tertiary amyl ether (TAME) isopentene boils within 6° F. of pentene-1 and 2-methyl-1-butene. Again, alkylating isopentanes to remove them as heavier products reduces or eliminates the requirement for venting isopentane and the subsequent carryover loss of pentene isomers that are beneficially used to produce additional TAME product. Therefore, a major advantage of this invention is the preservation of isoalkene and normal alkene isomers by the balanced consumption of isoalkane isomers between etherification and alkylation process steps. Additional advantages of this invention include a flow scheme that balances the production of ethers with other high octane gasoline blending components to suit changing requirements for oxygenate demands in gasoline products. Preferred aspects of this invention also include minimization of hydrogen addition to the process and simplified means for controlling hydrogen circulation throughout the process.

Therefore, it is an object of this invention to vary the product between an alkylation zone and an etherification zone to maintain a desired balance of oxygenates in a gasoline product.

It is a further object of this invention to reduce the loss of isoalkenes and other valuable alkene isomers by using alkylation to consume isobutane in an integrated process.

Another object of this invention is the elimination of equipment and processing steps for the addition of hydrogen to hydroprocessing steps.

Accordingly in one embodiment this invention is a process for the production of ether and alkylate from a feedstream including $C_4$ to $C_5$ normal alkene, isoalkene, normal alkane and isoalkane isomers. The process mixes an etherification input stream comprising $C_4$ to $C_5$ isoalkenes, normal alkenes, isoalkanes, and normal alkanes with a $C_1$–$C_5$ monohydroxy alcohol to produce a combined feed and contacts the combined feed with an etherification catalyst in an etherification zone at etherification conditions to react the isoalkenes with the alcohol and produce an etherification effluent stream comprising ether and isoalkane, normal alkane, and normal alkene isomers. A separation zone receives a separation zone input stream comprising at least a portion of the etherification effluent stream and including normal alkane, normal alkene and isoalkane isomers and provides a high boiling first fraction comprising the ether from the separation zone, and a second fraction comprising the isoalkane, normal alkene and normal alkane isomers. The separation zone passes a first portion of the second fraction to an alkylation zone and contacts the second stream with an alkylation catalyst at alkylation conditions to produce an alkylate product stream comprising high octane motor fuel components. A second portion of the second stream passes to an isomerization reaction zone for the skeletal isomerization of normal alkenes and contacts the second portion of the second stream with an isomerization catalyst at isomerization conditions. The isomerization zone passes at least a portion of an isomerization zone effluent stream comprising isoalkenes to the etherification reaction zone to provide at least a portion of the etherification reaction zone feedstream. Feed enters the process by passing the feedstream, including normal alkene, isoalkene, normal alkane and isoalkane isomers into at least one of the etherification zone, the separation zone and the isomerization zone.

Additional aspects of this invention relate to the arrangements required for distillation of feedstreams, reaction zone locations and treatment zones. In particular, another aspect of this invention is the reaction of unsaturated $C_4$ hydrocarbon isomers to produce MTBE and the reaction of unsaturated $C_5$ isomers for the production of methyl tertiary amyl ether. Other aspects of this invention include additional means for separation such as passing the isomerization zone effluent to a separation column to remove an overhead stream of saturated $C_4$ hydrocarbons, heavier $C_8$–$C_{10}$ hydrocarbons produced by dimerization and an intermediate stream containing the isoalkenes for input to the etherification zone. Additional separation steps can include an oxygenate recovery zone that uses distillation to separate saturated isoalkane isomers along with the oxygenates removed from the etherification effluent stream. Another separation system that may be incorporated into this invention separates the etherification effluent stream after separation of ethers into at least higher boiling and lower boiling streams. The lower boiling stream, rich in normal alkene isomers, passes to the isomerization zone as a feedstream. The entire higher boiling fraction of the ether deficient etherification zone effluent stream may enter the alkylation zone as feed or may first undergo separation for removal of higher boiling normal alkene isomers that return to the isomerization reaction zone with the lower boiling stream. The invention also uses a selective hydrogenation reaction to hydrogenate diolefins to monoolefins and to perform double bond isomerization of pentene isomers which reduces olefin losses by reacting them to TAME and thereby reducing the concentration when separating isoalkanes for venting or conversion. The separation zone of this invention may also provide reactive distillation to enhance the conversion of product and the recovery of potential reactants. The following derailed description of the invention sets forth additional details, embodiments, and aspects of the invention.

BRIEF DESCRIPTION OF THE DRAWING

The FIGURE is a schematic illustration of a process of this invention showing the etherification zone, isomerization zone, separation zone, and alkylation zone along with additional separators, and treating zones for the purification of the feedstream and product.

DETAILED DESCRIPTION OF THE INVENTION

This invention is broadly applicable to the production of a wide variety of ethers from a number of different feedstocks. The primary ethers for which this invention will be applied are tertiary amyl and butyl ethers. The advantages of this invention are achieved when the feedstream includes a mixture of normal and branched alkene and alkane isomers. Where the etherification process is one for the production of butyl ethers, the typical feedstream will consist of a mixture of $C_4$ isomers comprising isobutane, isobutene, normal butane, 1-butene and 2-butene. Where the process is one for the production of amyl ethers, the feedstream components will include 3 methyl-1-butene, isopentane, 1-pentene, 2 methyl-1-butene, normal pentane, trans-2-pentene, cis-2-pentene and 2 methyl-2-butene in a typical distribution of isomers. Since in the combination of etherification and skeletal olefin isomerization processes, the alkanes are not reacted to any significant degree, these components increase the amount of material that passes through the process and must be removed to prevent an unacceptable build-up of unreacted products that circulate through the process. Although a variety of sources are available to provide such feedstreams, the most common source of the feedstreams for these processes are light cracked hydrocarbon streams from an FCC unit, or a $C_4$ stream from a steam cracker after butadiene extraction or after the selective hydrogenation of butadiene to normal butenes.

Often these hydrocarbon streams will contain diolefins in addition to the desired monoolefin feed components. These diolefins interfere with the operation of the catalyst in downstream processes by polymerizing and forming heavy hydrocarbon compounds that block the active sites of the catalyst and prevent their use. Preferably, feedstreams for this process will undergo treatment for the elimination of diolefins. A common method of eliminating diolefins is by the selective hydrogenation of the diolefins to saturate the diolefins into monoolefins while preserving monoolefins. Those skilled in the art know a variety of selective hydrogenation processes for the saturation of diolefins to monoolefins. A particular catalyst and operating conditions for such selective hydrogenation processes can be found in U.S. Pat. Nos. 4,695,560 and 4,734,540 the contents of which are hereby incorporated by reference. The selective hydrogenation process typically employs a nickel on aluminum catalyst or a noble metal, such as palladium on alumina, for the selective hydrogenation. The nickel and/or palladium may be sulfided or unsulfided. The process can also operate at a broad range of operating conditions including pressures of from 40 to 800 psig with pressures of between 50 and 300 psig being preferred and temperatures of from 70°–700° F. with temperatures of from about 120°–400° F. being preferred. Effective space velocities for the processes should be above 1 $hr^{-1}$ and preferably are above 5 with a range of from between 5 to 35 $hrs^{-1}$. It is typical in such processes to limit the mount of hydrogen to prevent the saturation of monoolefins such that there is less than 2 times the stoichiometric mount of hydrogen required for the selective hydrogenation in the process. Preferably, the mol ratio of hydrogen to diolefinic hydrocarbons in the material will be in a range of from 1:1 to 1.8:1, and in some cases the hydrogen will be less than stoichiometrically required amount of hydrogen. Additional information related to the selective hydrogenation of diolefinic hydrocarbons, and in particular can be found in U.S. Pat. No. 4,695,560.

The feed to the process includes an alcohol to react with the isoolefin and produce the desired ether product. The alcohols that can be used are typically $C_1$–$C_5$ monohydroxy alcohols. Methanol typically constitutes the alcohol of choice for the etherification process. Ethanol, although used less commonly, is also a commonly available alcohol for the etherification process. Methanol is preferred somewhat since it is a stable commercial chemical of long standing.

The isoalkene as well as the normal alkene hydrocarbons will enter the etherification zone along with the alcohol. Contact with the etherification catalyst at etherification conditions will produce the ether product. A wide range of materials are known to be effective as etherification catalysts for the isoalkene reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. A particularly preferred etherification catalyst is a macroporous acid form sulfonic ion exchange resin such as a sulfonated styrene-divinylbenzene resin as described in U.S. Pat. No. 2,922,822 having a degree of crosslinking of from about 5 to 60%. Suitable resins are available commercially. Specialized resins have been described in the art and include copolymers of sulfonyl fluorovinyl ether and fluorocarbons as described in U.S. Pat. No. 3,849,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 $m^2/g$, a pore volume of 0.6–2.5 ml/g and a mean pore diameter of 40–1000 angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification calalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. Processes operating with vapor or mixed phase conditions may be suitably employed in this invention. The preferred etherification process uses liquid phase conditions or mixed liquid phase conditions in a catalytic distillation arrangement.

The range of etherification conditions for processes operating in liquid phase still includes a broad range of suitable conditions including a superatmospheric pressure sufficient to maintain the reactants as a liquid phase, generally below about 700 psig, and a temperature between about 85° and about 210° F. Even in the presence of additional light materials, pressures in the range of 140 to 580 psig are sufficient. A preferred temperature range is from 100°–210° F. The reaction rate is normally faster at higher temperatures but conversion is more complete at lower temperatures due to favorable thermodynamic equilibrium. High conversion in a moderate volume reaction zone can, therefore, be obtained if the initial section of the reaction zone, e.g., the first two-thirds, is maintained above 160° F. and the remainder of the reaction zone is maintained below 120° F. This may be accomplished most easily with two reactors. The ratio of feed alcohol to isoolefin should normally be maintained in the broad range of 1:1 to 2:1. With the isobutene and isopentene reactants, good results are achieved if the ratio of methanol to isobutene is between 1.05:1 and 1.5:1. An excess of methanol, above that required to achieve satisfactory conversion at good selectivity, should be avoided as some decomposition of methanol to dimethyl ether may occur which may increase the load on separation facilities. Various etherification process techniques, reaction conditions and product recovery methods are described in U.S. Pat. No. 4,219,678 to Obenaus et al. and U.S. Pat. No. 4,282,389 to Droste et al. which are incorporated herein for this teaching.

The etherification zone operates selectively to principally convert only the isoolefins. Etherification zones normally obtain high isoalkene conversion which for $C_5$ hydrocarbons will usually exceed 95% and $C_4$ hydrocarbons will typically exceed 98%. Therefore, alkanes and normal alkenes pass through the etherification zone without any significant conversion to products or by-products. Thus, the etherification zone effluent together with the unreacted feed components provides a stream of ether product and normal and branched alkene and alkane isomers for separation. In most cases, the stream entering the separation zone will also contain unreacted alcohol. The separation zone receiving the ether products, alcohol and unreacted alcohol distills the product into three separate boiling point fractions. Similar to most separation systems for recovery of ethers, the product separation zone provides a high boiling fraction that principally contains ether product. The product separation zone of this invention separates the remaining lower boiling components into a low boiling fraction containing isoalkane, normal alkenes, and normal alkanes that were not reacted in the etherification process or enter the separation zone directly as part of the process feed. Isoparaffins typically provide the lowest boiling constituent of the alkene and alkane isomers. While the isoalkanes can be conveniently withdrawn as a low boiling fraction from the separation zone, the purging of the isoalkane material results in the loss of valuable alkene materials or high capital and utility costs for a high recovery fractionation section.

In a continuously circulating process of this invention, the normal alkanes must also find a path out of the process loop in order to prevent their build-up. Typically, this process arrangement will withdraw a portion of the normal alkanes with the low boiling fraction from the separation zone. Withdrawal of the normal alkanes with the low boiling fraction establishes an equilibrium concentration of normal alkanes that was previously purged from the process since the normal alkene and alkane hydrocarbons present were usually suitable gasoline components. This invention makes better use of the normal alkene components ordinarily rejected with the normal alkanes.

As in most etherification arrangements, the low boiling fraction will also undergo methods for recovering the unreacted alcohol from the etherification zone. The etherification zone ordinarily operates with a high excess of alcohol to obtain the substantially complete conversion of isoalkenes. Those skilled in the art are familiar with the various azeotropes formed by the ether products and alcohol and can provide suitable means for such separations and recoveries. As anticipated for most cases, methanol will be the usual alcohol and any low boiling point fraction or intermediate boiling point fraction will ordinarily undergo an alcohol recovery step. Water washing provides the usual means for recovering methanol in such arrangements.

Following etherification and oxygenate separation, a portion of the unreacted alkenes from the etherification zone undergo skeletal isomerization of the normal alkenes to produce additional isoalkenes for the etherification process and another portion undergoes alkylation to consume isoalkanes and react normal alkenes that leave the process with rejected isoalkanes. In order to maintain catalyst stability in the isomerization or alkylation zone and to decrease acid consumption and unreacted by products in an HF or sulfuric acid catalyzed alkylation zone, the streams entering these zones often require removal of polar contaminants such as sulfur, nitrogen or oxygen compounds. Thus, in addition to processing for the recovery of methanol, the intermediate boiling fraction may also require additional purification for the removal of compounds that can poison the catalyst or interfere with the skeletal isomerization or alkylation processes. Depending on the type of isomerization catalyst, compounds that are usually most harmful to the isomerization catalyst include water, oxygenate compounds and nitrogen compounds. The water and oxygenate compounds may suppress the isomerization catalyst activity. The nitrogen compounds also affect the isomerization catalyst activity and results in a reduced activity. These nitrogen compounds are also poison to acidic ion exchange resins used for the etherification and thus are also beneficially removed prior to the etherification. A variety of methods are known to remove such compounds which include water washing, adsorption and extraction processes. Oxygenate compounds and nitrogen compounds can be removed by typical adsorbents for the removal of these contaminants which comprise zeolitic molecular sieves. Suitable types of zeolites are faujasites having pore sizes of about 10 angstroms. In particular, such zeolites include X, Y and L types as described in U.S. Pat. Nos. 3,216,789; 2,882,244 and 3,130,007. A particularly preferred type of zeolite is 13X. The use of type 13X sieves for the removal of oxygenate compounds such dimethyl ethers from the effluent from an etherification process is described in U.S. Pat. No. 4,814,517, the contents of which are hereby incorporated by reference. Suitable operation of the isomerization zone will require the removal of water and oxygenate compounds to a level of less than 50 wppm, and preferably less than 5 wppm water equivalents. Common nitrogen and oxygenate compounds that have also been found in light cracked products from an FCC unit include acetone and acetonitrile. These compounds are preferably removed by water washing such feeds prior to introduction into the process.

Different types of purification zones, referred to herein as oxygenate recovery zones, will have different effects on the way in which the process is used to reject the normal alkane and isoalkane isomers. Adsorptive type oxygenate recovery zones usually use a selective adsorbent that will limit the type of compounds removed from the stream to oxygenates and other contaminants. As a result, isoalkanes will remain with the purified hydrocarbon stream. Therefore, the use of an adsorptive oxygenate removal zone is preferred in those cases where the feedstream contains a relatively low concentration of isoalkane which is needed for reaction in the alkylation zone as hereinafter described. Conversely, distillation type oxygenate recovery zones will ordinarily remove isoalkanes especially isobutane along with the oxygenates and other contaminants distilled from the etherification zone effluent. This type of arrangement is preferred where the feedstream contains relatively high concentration of isoalkanes which would ordinarily exceed the amount of isoalkane needed in the alkylation zone for the reaction. Therefore, in its preferred aspects, this invention uses an oxygenate removal zone most suited for the isobutane content of the feedstream entering the process. Following purification of the etherification zone effluent stream for removal of alcohols, oxygenates and other contaminants, a portion enters an alkylation zone. Solid bed or liquid acid catalyzed alkylation zones such as sulfuric and HF processes are suitable for use in this invention. The preferred alkylation zone of this invention will be liquid acid catalyzed alkylation zone which provides a substantially complete conversion of olefins to higher weight hydrocarbons. The processes for hydrofluoric acid catalyzed alkylation are described in U.S. Pat. Nos. 4,795,728 and 4,665,271, the contents of which are hereby incorporated by reference. The selective hydrogenation zone of this invention is particularly important when using a hydrofluoric acid catalyzed alkylation process since diolefins when they are present tend to form high boiling hydrocarbons that increase the rate of HF acid consumption. In addition, the selective hydrogenation zone is desirable since it isomerizes butene-1 to butene-2. Butene-2 is a more desirable feed to the alkylation zone since it forms higher octane components such as 2,2,4-trimethylpentane. Although any type of alkylation reaction can be used, it is anticipated that an HF alkylation type process will be employed. In this type of process, the feed entering the alkylation reactor section should be dry and have a low sulfur content in order to reduce acid consumption and improve the quality of alkylate products. Water is eliminated since it causes corrosion problems in the acid environment. The acid is maintained in a liquid phase containing a minimum of water. The maximum amount of water normally allowed in the acid is about 5 wt. %. When fresh acid is charged to a plant, it is normally very dry and contains about 0.5% water or less. Methods for treating feeds for sulfur removal are well known. Standard practice for drying the feed has employed desiccant drying systems. As an alternative to the desiccant or other drying system, an alkylation feed stripper may also be used to dry the entire feed passing to the alkylation reactor.

Alkylation conditions in general include a pressure sufficient to maintain the hydrocarbons and acid in a liquid phase, with a general range being from about 140 kPag (20 psig) to about 3500 kPag (500 psig), and a more preferred range being from 700 kPag (100 psig) to about 1700 kPag (250 psig). It is preferred that the pressure within the reactant-catalyst contacting vessel is approximately 1050 kPag (150 psig) and essentially "floats" on the pressure maintained in downstream fractionation facilities. Although the alkylation reaction may be performed at temperatures from below −18−C. (−4° F.) to about 90° C. (195° F.), it is preferred to operate the commercially prevalent isoparaffin-olefin alkylation process in the range of from about 10° C. (50° F.) to about 60° C. (140° F.), with 32° C. (90° F.) being a representative and particularly preferred operating temperature.

Typically operating conditions in the alkylation zone include a high ratio of the concentration of the paraffinic or other alkylatable material to the concentration of the olefinic material in order to produce a high quality alkylate by encouraging monoalkylation instead of polymerization. A broad range for this ratio is from about 6 to about 20 with a preferred operating range being from 7 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.2:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They would, however, have substantial differences in equipment and flow paths used in performing the alkylation. These variations are well known to those skilled in the art and are attempts to obtain optimum quality alkylate by varying the method of contacting the monoolefin with the isoparaffin. Further details on the design and operation of reaction vessels, the overall operation of the alkylation step, the regeneration of the preferred HF calalysts, etc., are well known to those skilled in the art.

The other part of the normal alkene-rich input stream, after purification, enters the isomerization zone. (The term rich when used herein means a stream having a weight or volume percent content of at least 50% of the mentioned component while the term relatively rich means a stream having a higher concentration of the mentioned component than the feed from which it was derived.) Methods for converting the normal alkene components to isoalkene components by isomerization are known in the art. A process for converting linear alkenes to isomerized alkenes using a crystalline or silicate molecular sieve is taught in U.S. Pat. No. 4,503,282. Additional catalyst and methods for the skeletal isomerization of linear alkenes are described in U.S. Pat. Nos. 4,778,943 and 4,814,519. A preferred catalyst for the isomerization reaction zone of this invention is a non-zeolitic molecular sieve. Preferred forms of the non-zeolitic molecular sieve for this invention includes silicoaluminophosphates and a magnesium aluminophosphate. Suitable non-zeolitic catalysts such as the SAPO and MgAPSO are described in U.S. Pat. Nos. 4,440,871 and 4,758,419 which are hereby incorporated by reference. The catalyst for the isomerization zone typically lies in a fixed bed arrangement. In order to permit in-situ regeneration, the isomerization zone may include multiple reactors in a swing bed arrangement. Preferably, the reactants contact the catalyst in a vapor phase flow. Contacting a linear alkene feed with a catalyst in the presence of hydrogen in a molar ratio of from about 0.01 to 9, and preferably in a ratio of from 0.03 to 4, aids the process by suppressing the formation of carbon compounds on the catalyst. The isomerization process will typically operate over a broad range of conditions including temperatures of from 120°–1300° F. with temperatures in the range of 200°–1000° F. being preferred. Pressures for the isomerization reaction will also vary over a wide range extending from vacuum conditions to 700 psig, and preferably are in a range of 50 to 350 psig. Space velocities can also vary over a wide range from 0.5 to 100 hr$^{-1}$ with a preferred range of 1–5 hr$^{-1}$. The expected per pass conversion of normal alkenes to isoalkenes in the isomerization zone will generally reach at least 30% of the total combined feed entering the reaction zone and will more typically exceed 40%.

The effluent stream from the isomerization zone containing isoalkenes normally undergoes separation for the recovery of light gases including hydrogen. Hydrogen recovered in the light gases from the isomerization zone is recycled to the inlet of the isomerization zone to provide any necessary hydrogen concentration. The effluent from the isomerization zone may also undergo additional separation to remove additional light ends or reject heavier by-product hydrocarbons. Heavy materials such as $C_6^+$ olefinic hydrocarbons tend to foul or deactivate the isomerization catalyst. The presence of light ends in the isomerization zone effluent passes this light material on to the etherification zone as uncondensibles that, when rejected from the etherification separation system, drag methanol into downstream facilities thereby causing corrosion problems and methanol loss. A typical full separation zone then will include a first hydrogen separator that returns hydrogen to the isomerization process for admixture with the feed entering the isomerization zone. The effluent from the hydrogen separator will enter a second column that removes light ends as an overhead and will typically remove $C_6$ and higher molecular weight hydrocarbons as a bottoms stream. A side-cut fraction from the splitter column will normally be rich in isoalkenes and return to the etherification reactor ahead of the selective hydrogenation zone.

However, it is also possible to operate this process without any recovery of hydrogen or light ends from the skeletal isomerization zone. Therefore, in a simplified version of this process, the effluent from the isomerization reaction zone will either go at least in part directly to the etherification zone or can be passed directly to the etherification zone after separation of any recycle hydrogen. Operation of the invention with no hydrogen or with a low amount of hydrogen is particularly advantageous since it eliminates the compressors and separators associated with hydrogen recycle and can provide all of the hydrogen necessary for the upstream selective hydrogenation zone.

In the simplest arrangement of this invention, the effluent from the isomerization zone, after any separation, is admixed with the feed to the etherification zone to provide additional isoalkene reactants. The return of the isomerization effluent to the etherification reaction provides a loop incorporating components that are recycled through the process. Preferably, the feedstream of mixed, branched, and normal alkenes and alkanes will enter the process at a point in the loop just ahead of the etherification reaction zone. However, this feedstream may be added at a number of different points, depending on its composition, within this loop. For example, it is also possible to add the feedstream at a point just ahead of the isomerization zone or alkylation zone. In this way the total flow of reactants through the etherification zone is reduced by eliminating non-reactive isoalkane hydrocarbons. Those skilled in the art are aware of the particular characteristics of the feedstream and the desired product streams that will dictate the most advantageous location for introducing the feedstream.

Regardless of where the feedstream is added to the process, it is an essential part of this invention that the unreacted hydrocarbons from the etherification zone be split between the isomerization reaction zone and the alkylation reaction zone. In simplest form the split of these unreacted components may be a simple division of the effluent from the methanol recovery zone or the oxygenate recovery zone. As mentioned previously, an important consideration in this invention is obtaining a balance of isoalkane and alkene isomers so that the alkene isomers are fully reacted in the alkylation zone and used to their greatest advantage. In that way only normal alkanes are rejected from the process without octane and vapor pressure upgrading. The proportion of unreacted components sent to the alkylation zone depends on the concentration of isobutane entering the process and circulating throughout the process. In most cases approximately 10 to 50 wt. % of the unreacted components are sent to the alkylation zone. The split between the isomerization zone and the alkylation zone will preferably establish an equilibrium concentration of isobutane in the unreacted components such that the build up of isobutane provides a balanced concentration of isoalkane and alkene isomers for the alkylation zone. Preferably the mole ratio of isoalkanes to alkene isomers entering the alkylation zone will be in a range of from 3 to 10. As previously mentioned, an oxygenate recovery zone can provide some rejection of isoalkanes particularly isobutane. In cases where the isoalkane concentration is particularly high, additional rejection can be obtained by rejecting isoalkanes in a separate column upstream of the alkylation zone or by rejection from the overhead of the isomerization effluent splitter if provided.

Since the object of this invention is to reject normal alkanes as well as isoalkanes it may be useful to further separate the unreacted etherification fraction entering the alkylation zone in a separation zone. Therefore, in one arrangement the input stream entering the alkylation zone first passes into a separator that splits the input stream to produce an overhead fraction relatively rich in normal alkanes that enters the alkylation reaction zone and a bottom stream relatively rich in normal alkenes that passes directly to the isomerization reaction zone. Where the input fraction to the alkylation zone receives prior removal of isoalkanes either through an oxygenate recovery zone or other separation methods, it may be desirable to perform a further separation of the normal alkane rich stream from the alkylation zone input separator. The normal alkane rich stream may be further separated into a stream relatively rich in normal alkenes which passes directly to the isomerization zone and another fraction relatively rich in normal alkanes which again enters the alkylation zone. The removal of isoalkanes from the alkylation zone input stream prior to entering the separation zone is essential to prevent a high carryover of isobutane into the isomerization zone. When isoalkanes are withdrawn by the oxygenate removal zone it may be necessary to recycle isoalkanes to the alkylation zone to provide the proper reactant balance.

A better understanding of this invention may be obtained by reference to the FIGURE which shows a schematic arrangement for the process that does not include pumps, compressors, heat exchangers, coolers and other such necessary processing equipment, the provision of which is well known to those skilled in the art. In this example a cracked gasoline comprising $C_9$ through $C_4$ and lighter hydrocarbons enter a deisopentenizer 10 by feed stream 12. An overhead stream 14 carries $C_5$ and lighter hydrocarbons through a treatment zone 13. Treatment zone 13 can be a water wash zone or other treating zone that removes dilitarious components from the feed stream such as sulfur, nitrogen and oxygen compounds. Line 15 carries the treated feed into admixture with an isomerization zone effluent fraction comprising $C_5$ hydrocarbons carried by line 16. The combined stream passes into a selective hydrogenation zone 17 by a line 18. The selective hydrogenation zone saturates diolefins to monoolefins and performs double bond isomerization on 3-methyl-1-butenes to produce 2-methyl-2-butenes. Hydrogen as required enters the selective hydrogenation process through a line 20. Line 22 carries the substantially diolefin free feed stream into admixture with methanol carried by line 24. An etherification zone 26 can produce MTBE or TAME. In the the case of MTBE production the reaction zone converts isobutene and methanol. When producing TAME, etherification zone 26 reacts 2-methyl-2-butenes and 2-methyl-1-butenes, by contact with an etherification catalyst, into the TAME product which exits the reactor via line 28. Ether products separator 30 splits the etherification zone effluent into a bottom stream 32 that contains the ether product and an overhead steam 34 which, when producing TAME, comprises unreacted alcohol, isopentane, normal pentane and normal pentenes. A water wash column 36 removes methanol from the overhead 34 and provides a recycle stream of methanol carried by a line 38 which, after the addition of make up methanol via line 40, provides the contents of line 24. The isopentane, normal pentane and normal pentenes are carried via line 44 into an absorptive oxygenate removal zone 46. The purified stream exits zone 46 via a line 48 that splits into an isomerization zone feed carried by line 50 and an alkylation zone feed carried by line 52. Make up hydrogen, if necessary, is admixed with the contents of line 50 by line 51. Line 56 feeds optional recycle hydrogen into a line 58 that receives the contents of line 50 and transfers the isomerization zone input stream into an isomerization reactor 60. Line 61 passes the effluent from isomerization zone 60 to hydrogen separator 62 that provides recycle hydrogen carried by line 56. The hydrogen deficient bottom stream taken by a line 64 enters a separator 66 that produces a stream of light end material comprising isopentene and lower boiling hydrocarbons taken overhead by line 68 and a stream of relatively heavy hydrocarbons having 6 or more carbon atoms taken by line 70. A side cut from the column provides the isopentene rich stream supplied by line 16.

Isopentane and normal pentene carried by line 52 enter an alkylation zone 72. Alkylation zone 72 operates with a hydrofluoric acid catalyst which effects an essentially complete conversion of normal pentenes to $C_8$ and higher hydrocarbons. A line 74 carries the alkylation product into admixture with the ether product carried by line 32 to produce an oxygenated blended gasoline stream from the $C_5$ and lower hydrocarbons carried by line 76. The oxygenated gasoline stream carried by line 76 may be further combined with $C_6$ and heavier gasoline components taken from separator 10 by line 78 to produce a blended gasoline product carried by line 80.

As described previously, the input stream to the alkylation zone is susceptible to a number of different separations. The FIGURE shows an optional separator that carries the alkylation zone input stream via line 82 into the optional separator 84. When using optional separator 84 the oxygenate removal zone 46 operates with a distillation type process to additionally remove isopentanes via a transfer line 86. With the removal of isopentanes via line 86, separator 84 provides an overhead relatively rich in pentene-1 that enters line 50 via line 81. Separator 84 also provides additional pentene-2 isomers through a line 88 that transfers a bottom stream to line 50. Separator 84 provides the alkylation input stream as a side cut 90 normally rich in normal pentane and containing substantial quantities of transpentene. In this optional separator arrangement the isopentane from line 86 combines with the normal pentene and transpentene containing stream carried by line 90 to enter alkylation 72 via line 52'.

The FIGURE also shows optional arrangements for the isomerization zone. In one such arrangement the isomerization zone effluent is directly recycled to the etherification reactor without any separation via an optional line 92. In another arrangement the effluent is transferred after hydrogen separation via line 94.

EXAMPLES

A series of examples were calculated based on data from operating units and laboratory test results to show the operation of this invention. This example presents the operation of the isomerization zone of this invention in the context of an arrangement for the etherification of $C_4$ isomers with methanol to produce MTBE along with alkylate and isomerate. The table shows the relative stream compositions throughout the process when processing a $C_4$ stream with the stream numbers corresponding to those in the figures.

With reference to the FIGURE a $C_4$ feedstream after initial separation of the feed in splitter 10 and purification of the overhead in treatment zone 13 is combined with feed components from lines 16 and provides a combined feed having the composition given in the Table for line 18. In the selective hydrogenation reactor hydrogen and the contents of line 18 are contacted with a nickel catalyst on an alumina support. The effluent from the selective hydrogenation reactor has the composition given for stream 22 which passes in admixture with about 25 weight % of methanol added to the contents of line 22 by line 24. The combined feed from line 22 and 24 is contacted in etherification reaction zone 26 with a sulfonic acid resin catalyst at a temperature of 80° F. and a pressure of 100 psig. After separation in column 30 the ether product has a composition given in Table 1 for line 32. Following recovery of methanol and additional oxygenates in columns 36 and in oxygenates removal zone 46 the stream of unreacted $C_4$ hydrocarbons has the composition given for line 48. Approximately 20 weight % of stream 48 stream passes directly to alkylation unit 72. Alkylation unit 72 uses an HF acid catalyst to alkylate the feed stream and produce the product stream given for line 74. The remaining portion of stream 48 passes on to the isomerization reactor 60 where it is contacted with a silica alumina phosphate catalyst having a temperature of 300° to 1000° F. and a pressure of 10 psig to 300 psig. After recovery of hydrogen and separation of light ends, a fraction of the reactor effluent having the composition given for line 16 is returned to the etherification reaction zone. As can be seen, the feed to the alkylation zone has a ratio of butenes to isobutene of approximately 1.5. The amount of isobutene present in the reaction zone is more than adequate to fully react the isobutane to higher octane alkylate and remove isobutane from the process. More complete utilization of the butenes may be obtained by importing isobutane into the alkylation reaction zone 72.

TABLE 1

RELATIVE CONCENTRATION (WT-%)

| STREAM NO. | | | | | |
|---|---|---|---|---|---|
| | 18 | 22 | 32 | 48 | 16 |
| $H_2$ | 1.8 | | | | |
| $C_3$ | .2 | .2 | — | — | — |
| Isobutane | .5 | .45 | — | 35.2 | 26.9 |
| Isobutene | 22.9 | 21.3 | — | .3 | 19.5 |
| Butene-1 | 18.8 | 45.3 | — | 12.2 | 9.3 |
| 3-Butadiene | 48.1 | — | — | — | — |
| n-Butane | 2.79 | 3.6 | — | 12.4 | 9.5 |
| t-2-Butene & c-2-Butene | 9.4 | 28.8 | — | 39.6 | 30.2 |
| Misc. $C_4$ | 1.3 | — | — | — | — |
| $C_5$ | .1 | .1 | .3 | .1 | 1.4 |
| $C_6^+$ | — | — | 8.7 | — | 3.0 |
| TBA | | | 1.3 | — | — |
| TAA | | | .1 | — | — |
| MEOH | — | — | — | | |
| DME | | | — | — | — |
| TAME | | | 4.8 | — | — |
| MTBE | | | 84.7 | — | — |

What is claimed is:

1. A process for the production of ether and alkylate from a feedstream including $C_4$ to $C_5$ normal alkene, isoalkene, normal alkane and isoalkane isomers, said process consisting of:

(a) mixing an etherification input stream comprising $C_4$ to $C_5$ isoalkenes, normal alkenes, isoalkanes, and normal alkanes with a $C_1$–$C_5$ monohydroxy alcohol to produce a combined feed and contacting said combined feed with an etherification catalyst in an etherification zone at etherification conditions to react isoalkenes with said alcohol and produce an etherification effluent stream comprising ether and isoalkane, normal alkane, and normal alkene isomers;

(b) passing a separation zone input stream comprising at least a portion of said etherification effluent stream and including normal alkane, normal alkene and isoalkane isomers to a first separation zone, distilling said separation input stream to separate ether from said separation zone input stream and withdrawing a high boiling first stream comprising said ether from said separation zone, and a second stream comprising said isoalkane, normal alkene and normal alkane isomers;

(c) passing a first aliquot portion of said second stream equal to 10 to 50% of said second stream to an alkylation zone and contacting said first aliquot portion stream with an alkylation catalyst at alkylation conditions to produce an alkylate product stream comprising high octane motor fuel components;

(d) passing a second aliquot portion of said second stream to an isomerization reaction zone for the skeletal isomerization of normal alkenes and contacting said second portion of said second stream with an isomerization catalyst at isomerization conditions;

(e) withdrawing an isomerization zone effluent stream comprising isoalkenes from said isomerization zone and passing at least a portion of said isomerization zone effluent to said etherification reaction zone; and, (f) passing said feedstream including normal alkene, isoalkene, normal alkane and isoalkane isomers into at least one of said etherification zone, said separation zone and said isomerization zone.

2. The process of claim 1 wherein a portion of said feedstream enters said alkylation zone.

3. The process of claim 1 wherein a portion of said isomerization zone effluent enters a second separation zone and said second separation zone produces an overhead stream comprising $C_4$ and lighter hydrocarbon gases, a bottoms stream comprising $C_8$ and higher boiling hydrocarbons and an intermediate stream comprising isoalkenes and isoalkanes.

4. The process of claim 1 wherein said etherification input stream comprises normal butane, isobutane, normal butene, and isobutene.

5. The process of claim 1 wherein said etherification input stream comprises normal pentene, isopentane, normal pentene, and isopentene.

6. The process of claim 1 wherein said etherification input stream comprises normal butane, isobutane, normal butene, isobutene, normal pentene, isopentane, normal pentene, and isopentene.

7. The process of claim 1 wherein a portion of said etherification zone effluent and said alkylation zone effluent are combined with at least a portion of a higher boiling hydrocarbon fraction separated from said feedstream to provide a gasoline product stream.

8. The process of claim 1 wherein said etherification input stream passes through a selective hydrogenation reactor before entering said etherification zone and at least a portion of said isomerization effluent stream passes from said isomerization zone to said selective hydrogenation zone to supply hydrogen to said selective hydrogenation zone.

9. The process of claim 8 wherein said portion of said isomerization zone effluent stream passes directly from said isomerization zone to said selective hydrogenation zone without intermediate separation.

10. The process of claim 8 wherein said portion of said isomerization effluent stream supplies all of the necessary hydrogen for said selective hydrogenation zone.

11. The process of claim 1 wherein said second stream, passes through an oxygenate recovery zone and said oxygenate recovery zone removes oxygenates and isoalkane hydrocarbons from said second stream.

12. A process for the production of tertiary amyl ether and high octane gasoline blending components from a feedstream including normal pentane, isopentane, normal pentene, and isopentene, said process consisting of:
   (a) mixing said feedstream and an isomerization zone effluent stream to produce a combined feed and contacting said combined feed with a selective hydrogenation catalyst at selective hydrogenation conditions in a selective hydrogenation zone to saturate diolefins to mono-olefins and produce a hydrogenated combined feed;
   (b) contacting said hydrogenated combined feed and a $C_1-C_5$ monohydroxy alcohol with an etherification catalyst in an etherification zone at etherification conditions to react isopentenes with said alcohol and produce an etherification effluent stream comprising tertiary amyl ether, unreacted alcohol, normal pentene, normal pentene, and isopentane;
   (c) passing said etherification zone effluent stream to a separation zone, distilling said etherification zone effluent stream to separate ether from said etherification zone effluent stream and recovering a high boiling point first fraction comprising tertiary amyl ether and a second fraction comprising unreacted alcohol, isopentane, normal pentene and normal pentane;
   (d) passing said second fraction to an oxygenate removal zone to remove oxygenate compounds from said second fraction
   (e) passing an aliquot first portion of said second fraction equal to 10 to 50% of said second fraction from said oxygenate recovery zone to a an alkylation zone and contacting said first portion of said second fraction with an alkylation catalyst at alkylation conditions to produce an alkylate product stream comprising high octane motor fuel components;
   (f) passing an aliquot second portion of said second fraction from said oxygenate removal zone to an isomerization reaction zone for the skeletal isomerization of normal pentenes and contacting said second portion of said second fraction with an isomerization catalyst at isomerization conditions; and,
   (g) withdrawing an isomerization zone effluent stream comprising isopentenes from said isomerization zone and passing at least a portion of said isomerization zone effluent to said etherification reaction zone.

13. The process of claim 12 wherein said alcohol comprises methanol and said product comprises a methyl tertiary amyl ether.

14. The process of claim 12 wherein said selective hydrogenation isomerizes 3 methyl-1 butene to 2 methyl-2 butene.

15. The process of claim 12 wherein said isomerization zone effluent passes directly from said isomerization zone to a hydrogen separator and at least a portion of the higher boiling fraction from said separator passes to said selective hydrogenation zone without intermediate separation.

16. The process of claim 13 wherein said oxygenate removal zone also removes isopentane from said second fraction.

17. The process of claim 13 wherein said first portion of said second fraction is separated into a third fraction that is relatively rich in isopentane and a fourth fraction that is relatively lean in isopentane and said third fraction is passed to said alkylation zone and said fourth fraction is passed to said isomerization zone.

18. A process for the production of tertiary butyl ether from a feedstream including normal butene, isobutene, normal butane, and isobutane, said process consisting of:
   (a) mixing said feedstream and an isomerization effluent stream with a $C_1-C_5$ monohydroxy alcohol to produce a combined feed and contacting said combined feed with an etherification catalyst in an etherification zone at etherification conditions to react isobutenes with said alcohol and produce an etherification effluent stream comprising tertiary butyl ether, unreacted alcohol, normal butane, normal butene, and isobutane;
   (b) passing said etherification zone effluent stream to a separation zone, distilling said etherification zone effluent stream to separate ether from said etherification zone effluent stream and recovering a high boiling first fraction comprising tertiary butyl ether and a second fraction comprising unreacted alcohol, isobutane, normal butane and normal butene;
   (c) passing said second fraction to an oxygenate removal zone to remove oxygenate compounds from said second fraction;
   (d) passing an aliquot first portion of said second fraction equal to 10 to 50% of said second fraction from said oxygenate removal zone to an alkylation zone and contacting said first portion of said second fraction with an alkylation catalyst at alkylation conditions to produce an alkylate product stream comprising high octane motor fuel components;
   (e) passing a second portion of said second fraction from said oxygenate removal zone to an isomerization reaction zone for the skeletal isomerization of normal butenes and contacting said second portion of said second fraction with an isomerization catalyst at isomerization conditions; and,
   (f) withdrawing an isomerization zone effluent stream comprising isobutenes from said isomerization zone and passing at least a portion of said isomerization zone effluent to said etherification reaction zone to provide at least a portion of said etherification reaction zone feedstream.

19. The process of claim 18 wherein said alcohol comprises methanol and said product comprises a methyl tertiary butyl ether.

20. The process of claim 18 wherein said feedstream is contacted with a selective hydrogenation catalyst at selective hydrogenation conditions in a selective hydrogenation zone to selectively saturate diolefins to monoolefins.

21. The process of claim 20 wherein said isomerization zone effluent passes directly from said isomerization zone to a hydrogen separator and at least a portion of the higher boiling fraction from said separator passes to said selective hydrogenation zone without intermediate separation.

22. The process of claim 18 wherein said oxygenate removal zone also removes isobutane from said second fraction.

* * * * *

UNITED STATES PATENT AND TRADEMARK OFFICE
CERTIFICATE OF CORRECTION

PATENT NO: 5,672,795
DATED: Sep.30, 1997
INVENTOR(S): BIPIN V. VORA, TAMOTSU IMAI, and PETER R. PUJADO It is certified that error appears in the above-identified patent and that said Letters Patent is hereby corrected as shown below:

Claim 12, (b) line 21,

"normal pentene" should be - - normal pentane - -.

Signed and Sealed this

Sixteenth Day of December, 1997

Attest:

BRUCE LEHMAN

Attesting Officer

Commissioner of Patents and Trademarks